(12) United States Patent
Dickson

(10) Patent No.: US 10,206,666 B2
(45) Date of Patent: Feb. 19, 2019

(54) TISSUE BAG AND METHOD OF MORCELLATING TISSUE

(71) Applicant: GYRUS MEDICAL LIMITED, Cardiff (GB)

(72) Inventor: James Alan Dickson, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 289 days.

(21) Appl. No.: 15/046,659

(22) Filed: Feb. 18, 2016

(65) Prior Publication Data

US 2016/0242752 A1     Aug. 25, 2016

(30) Foreign Application Priority Data

Feb. 20, 2015   (GB) .................................. 1502837.6

(51) Int. Cl.
*A61B 17/00*       (2006.01)
*A61B 17/3205*    (2006.01)
(Continued)

(52) U.S. Cl.
CPC .. *A61B 17/00234* (2013.01); *A61B 17/32053* (2013.01); *A61B 17/32056* (2013.01); *A61B 17/42* (2013.01); *A61B 2017/00287* (2013.01); *A61B 2017/00557* (2013.01); *A61B 2017/00951* (2013.01); *A61B 2017/22051* (2013.01); *A61B 2017/22054* (2013.01); *A61B 2017/22055* (2013.01); *A61B 2017/320024* (2013.01);
(Continued)

(58) Field of Classification Search
CPC ... A61B 46/13; A61B 46/17; A61B 17/00234; A61B 17/32056; A61B 17/42; A61B 2017/00287; A61B 2017/220051; A61B 2017/220054; A61B 2017/320024; A61B 2017/320064; A61B 2017/4216
See application file for complete search history.

(56) References Cited

U.S. PATENT DOCUMENTS 5,037,379 A   8/1991 Clayman et al.
5,337,754 A   8/1994 Heaven et al.
(Continued)

FOREIGN PATENT DOCUMENTS

WO   94/13215 A1   6/1994
WO   98/09569 A1   3/1998

OTHER PUBLICATIONS

Search Report under Section 17(5) in U.K. Application No. GB1502837.6, dated Jul. 15, 2015.

*Primary Examiner* — Robert Lynch
(74) *Attorney, Agent, or Firm* — Oliff PLC

(57) ABSTRACT

A tissue bag for surrounding tissue (2) during a surgical procedure comprises a bag body (6) capable of forming an enclosure, an opening (9) in the bag body, and one or more inflatable ribs (8) located on the bag body. The ribs (8) are such that inflation of the one or more ribs to a first extent causes the bag to deploy to an open position in which the bag is capable of being placed over tissue with the tissue received through the opening. Inflation of the one or more ribs (8) to a second further extent causes the bag to envelop the tissue with the opening (9) being smaller in diameter than in the open position. The ribs may each include at least first and second discrete longitudinal portions (10), (11) with an angled end face (15) therebetween.

23 Claims, 5 Drawing Sheets

(51) Int. Cl.
  *A61B 17/42*   (2006.01)
  *A61B 17/32*   (2006.01)
  *A61B 17/22*   (2006.01)

(52) U.S. Cl.
  CPC .............. *A61B 2017/320064* (2013.01); *A61B 2017/4216* (2013.01)

(56) References Cited

U.S. PATENT DOCUMENTS

| | | |
|---|---|---|
| 5,618,296 A | 4/1997 | Sorensen et al. |
| 5,735,289 A | 4/1998 | Pfeffer et al. |
| 6,270,505 B1 | 8/2001 | Yoshida et al. |
| 8,430,826 B2 | 4/2013 | Uznanski et al. |
| 2011/0184432 A1* | 7/2011 | Parihar ............ A61B 17/00234 606/114 |

* cited by examiner

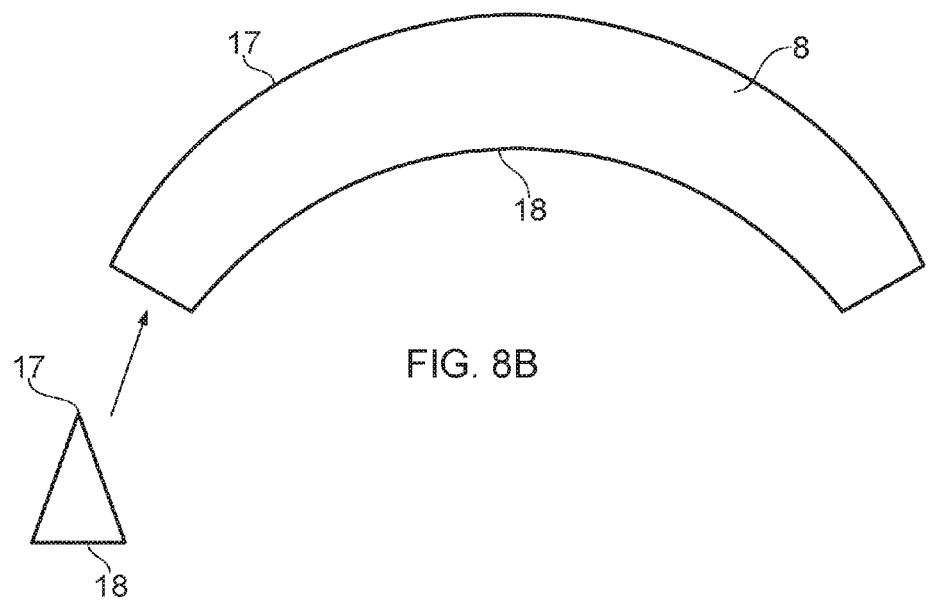
FIG. 8B
FIG. 8A
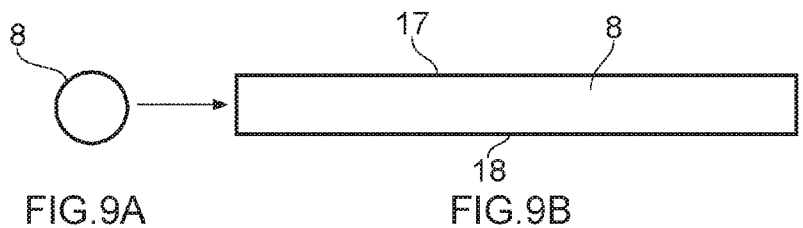
FIG. 9A    FIG. 9B
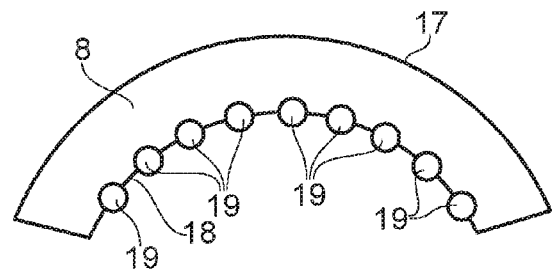
FIG. 9C

TISSUE BAG AND METHOD OF MORCELLATING TISSUE

TECHNICAL FIELD

Embodiments of this invention relate to a tissue bag for use in the encapsulation of tissue, and to a method for morcellating tissue such as a female uterus.

Background to the Invention and Prior Art

Due to the perceived risks associated with the "seeding" of cancerous tissue, the morcellation of tissue is often carried out in a tissue bag surrounding or containing the tissue. An example of such a tissue bag is given in U.S. Pat. No. 5,037,379. In the tissue bag of U.S. Pat. No. 5,037,379, a morcellating instrument is introduced into the bag in order to morcellate the tissue into smaller pieces before the bag is removed from the body of the patient. Other prior art examples of similar arrangements include those described in U.S. Pat. No. 8,430,826, and U.S. Pat. No. 5,337,754.

SUMMARY OF THE INVENTION

Embodiments of the present invention attempt to provide an improvement to the above described type of morcellation process. Accordingly, a tissue bag for surrounding tissue during a surgical procedure comprises a bag body capable of forming an enclosure, an opening in the bag body, and one or more inflatable ribs located on the bag body, the ribs being such that inflation of the one or more ribs to a first extent causes the bag to deploy to an open position in which the bag is capable of being placed over tissue with the tissue received through the opening, and that inflation of the one or more ribs to a second further extent causes the bag to envelop the tissue with the opening being smaller in diameter than in the open position.

The inflation of the one or more ribs first causes the tissue bag to open so as to enclose the tissue, and then further inflation causes the bag to close over the tissue enveloping it within the bag. The one or more inflatable ribs preferably extend longitudinally with respect to the opening. The longitudinal direction of the one or more ribs allows them to effect the shaping of the bag as it first encloses and then envelops the tissue. The inflation of the one or more ribs may also allow the tissue bag to manoeuvre itself between adjacent tissue structures, and may avoid the necessity for intervention with tissue graspers or the like.

Preferably, the tissue bag includes a plurality of inflatable ribs located on the bag body. In one convenient arrangement the tissue bag includes a plurality of inflatable ribs extending longitudinally at equally spaced intervals around the circumference of the tissue bag.

According to a first construction, the one or more inflatable ribs each include at least first and second discrete longitudinal portions. The first and second longitudinal portions are preferably conjoined by an end face disposed at a non-orthogonal angle to the longitudinal axis of the rib. The non-orthogonal end face between the portions causes the rib (and hence the tissue bag) to adopt a curved configuration so as to first enclose and then envelop the tissue. Preferably, the angle between the longitudinal axis of the first portion and that of the second portion is between 10 and 45 degrees, typically between 15 and 30 degrees, and preferably around 20 to 25 degrees.

Typically, the one or more inflatable ribs include at least first, second and third discrete longitudinal portions, again conveniently with the second and third discrete longitudinal portions being conjoined by an end face disposed at a non-orthogonal angle to the longitudinal axis of the rib. Once again, the angle between the longitudinal axis of the second portion and that of the third portion is typically between 10 and 45 degrees, typically between 15 and 30 degrees, and preferably around 20 to 25 degrees. The angled first, second and third portions, especially if repeated in a plurality of ribs spaced around the tissue bag, causes the bag to assume a shaped configuration as it is deployed, opening over the tissue and then enveloping it.

According to an alternative construction, the one or more inflatable ribs each include a longitudinal section with an upper and a lower surface, the upper surface being of a greater length than that of the lower surface. The difference between the length of the upper and lower surfaces causes the rib to assume a curved configuration as it is inflated, thereby providing the necessary guidance for the tissue bag to envelop the tissue one it has been located in position. Conveniently, the one or more inflatable ribs have a generally triangular cross-section. Typically, the base of the triangle constitutes the lower surface, and the apex of the triangle constitutes the upper surface.

According to a further alternative construction, the one or more inflatable ribs each have a generally circular cross-section. The one or more inflatable ribs each typically include a plurality of adhesions disposed along one longitudinal axis thereof. Conveniently, the adhesions are equally spaced along the longitudinal axis. The adhesions serve to ensure that one surface of the rib expands less readily than the other, causing the rib to assume a bent or curved shape when inflated. Typically, each of the adhesions is formed by applying a small amount of adhesive to the rib.

Whichever construction is employed, the one or more inflatable ribs are preferably such that they inflate to form an arc having a radius of between 5 cm and 15 cm, and preferably between 7 and 10 cm. This shape adopted when the rib is inflated, especially when reproduced by other ribs present on the tissue bag, helps to provide the tissue bag with its unique deployment regime.

Typically, the opening of the tissue bag is provided with a drawstring which can be pulled in order to close the opening. In this way, once the tissue bag has been deployed to enclose and envelop the tissue, the drawstring can be pulled in order to close the opening and capture the tissue within the bag. Conveniently, the tissue bag is mounted on an elongate introducer element capable of manipulating the tissue bag into position. The introducer element is preferably provided with a lumen through which an inflation gas can be supplied to the one or more inflatable ribs, in order to inflate them when required.

Embodiments of the invention further reside in a method of encapsulating tissue for surgical purposes, comprising the steps of i) introducing a tissue bag into the body of a patient, the tissue bag including a bag body capable of forming an enclosure, an opening in the bag body, and one or more inflatable ribs located on the bag body, ii) inflating the one or more ribs to a first extent such that the bag deploys to an open position, iii) placing the bag over the tissue to be enclosed, with the tissue being received through the opening, and iv) further inflating the one or more ribs to a greater extent such that the bag envelops the tissue with the opening being smaller in diameter than in the open position.

The method conveniently includes the further step of pulling a drawstring to close the opening once the ribs have been inflated to envelop the tissue.

Other embodiments of the invention further reside in a method of morcellating a uterus, comprising the steps of
  i) introducing a tissue bag into the body of a patient, the tissue bag including a bag body capable of forming an enclosure, an opening in the bag body, and one or more inflatable ribs located on the bag body,
  ii) inflating the one or more ribs to a first extent such that the bag deploys to an open position,
  iii) placing the bag over the uterus, with the uterus being received through the opening,
  iv) further inflating the one or more ribs to a greater extent such that the bag envelops the uterus with the opening being smaller in diameter than in the open position, and
  v) morcellating the uterus within the tissue bag.

DESCRIPTION OF THE DRAWINGS

Embodiments of the invention will now be further described, by way of example only, with reference to the accompanying drawings, in which FIG. 9A is a schematic cross-sectional view showing an inflatable rib according to an alternative embodiment of tissue bag according to the invention, FIG. 9B is a schematic side view of the rib of FIG. 9A in a generally non-inflated condition, and FIG. 9C is a schematic side view of the rib of FIG. 9A in an inflated condition.

DESCRIPTION OF THE EMBODIMENTS

Figure 1:
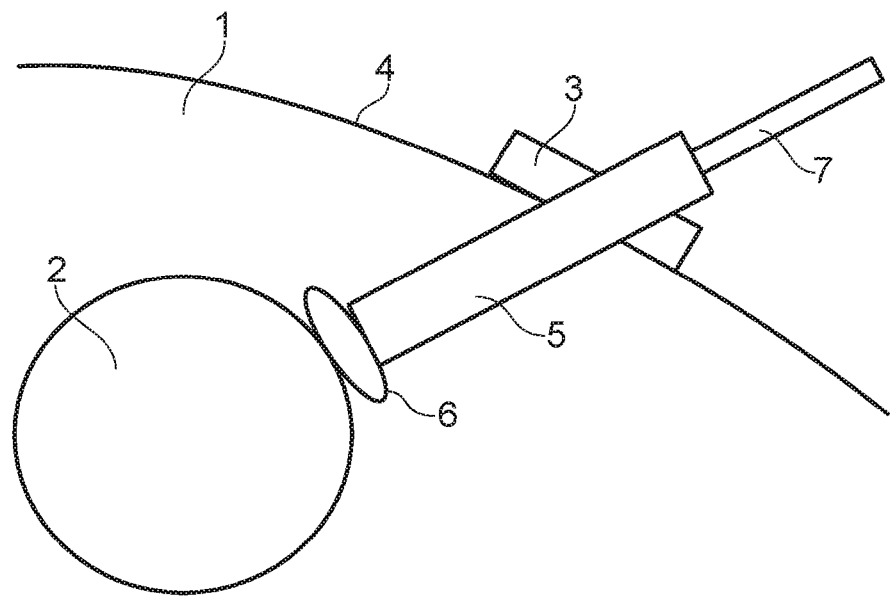
FIG. 1 is a schematic side view of a tissue bag in accordance with an embodiment of the present invention.

Referring to FIG. 1, a patient is shown generally at 1, with target tissue such as a uterus shown at 2. A port is shown at 3, inserted into the body 4 of the patient. Inserted through the port 3 is an introducer in the form of a hollow sleeve 5 with a tissue bag 6 mounted at its distal end. A tube 7 is provided to supply an insufflation gas through the sleeve 5 to the bag 6.

Figure 2:
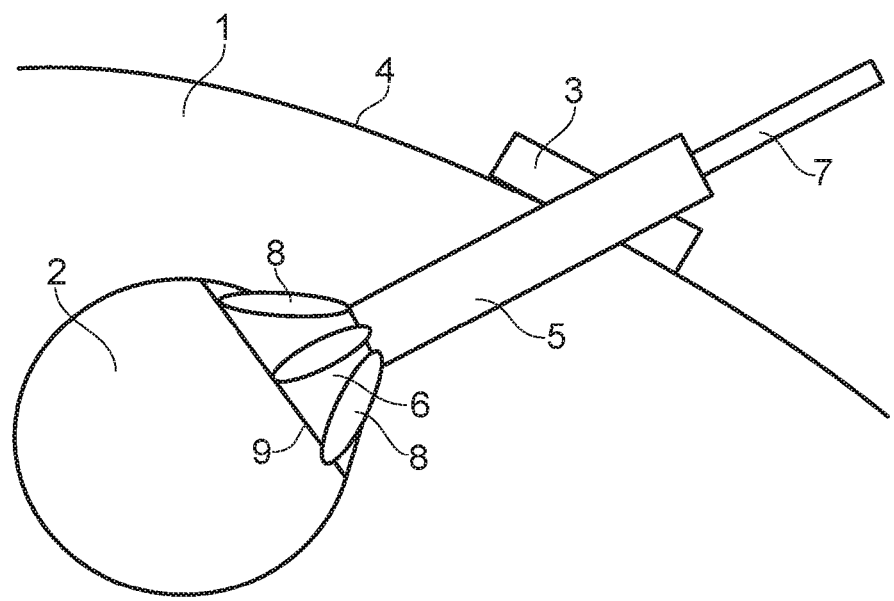
FIGS. 2 to 4 are schematic side views showing the tissue bag of FIG. 1 being placed over a female uterus.

The surgeon manipulates the sleeve 5 such that the tissue bag 6 is adjacent the uterus 2, and activates the supply of insufflation gas. The gas is supplied to a series of inflatable ribs 8 running longitudinally with respect to the bag 6. As the ribs 8 start to inflate, the bag 6 expands as shown in FIG. 2, with an opening 9 in the bag allowing the bag to start to enclose the uterus.

Figure 3:
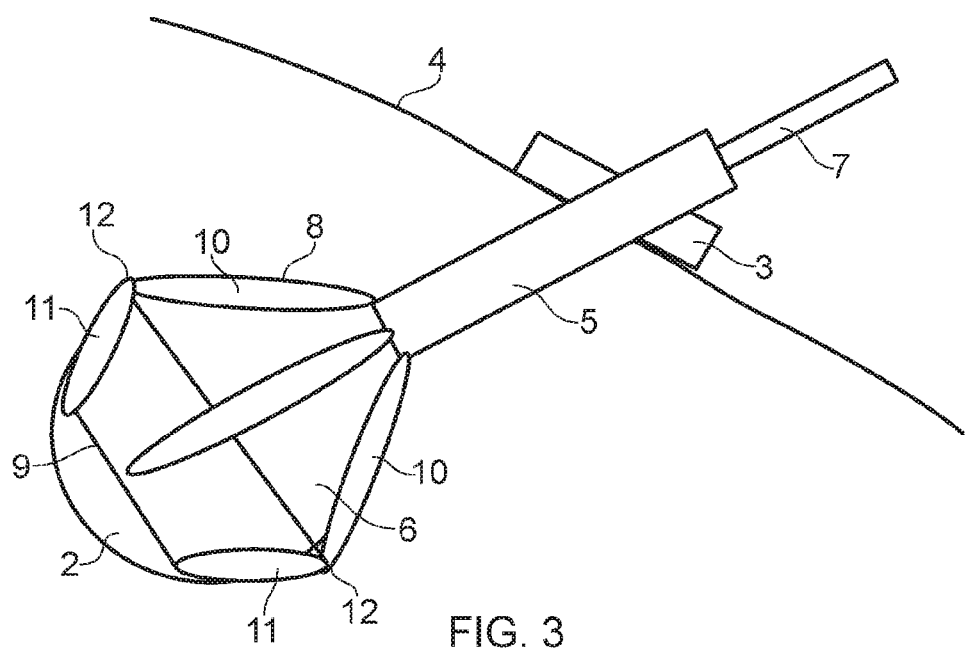

As the ribs 8 inflate further as shown in FIG. 3, each rib is formed of a first portion 10 and a second portion 11, with an elbow 12 therebetween. The second portions 11 of the ribs are deployed at an angle to the first portions 10, such that the tissue bag 6 adopts a generally spherical shape enfolding itself around the uterus 2 and generally enveloping it. The opening 9 becomes restricted due to the converging angle of the second portions 11 of the ribs 8, ensuring that the uterus 2 is captured within the bag.

Figure 4:
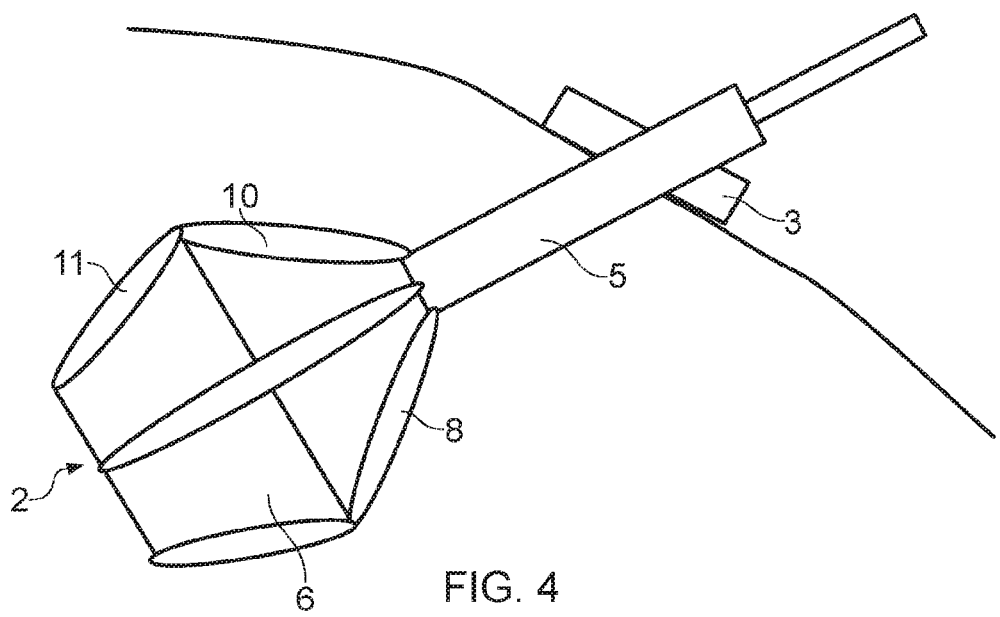
Figure 5:
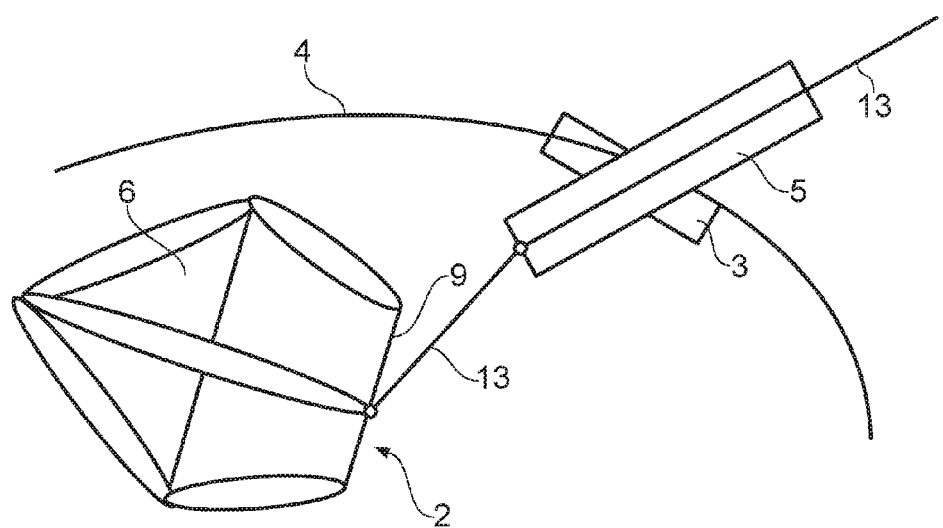
FIGS. 5 and 6 are schematic side views showing the tissue bag of FIG. 1 with a female uterus within the bag.

FIG. 4 shows how, when the ribs 8 are fully inflated, the tissue bag 2 fully envelops the uterus 2. The tissue bag can then be detached from the sleeve 5, and the tissue bag rotated as shown in FIG. 5, using a drawstring 13 attached to the opening 9 and running through the sleeve 5. The sleeve 5 may be unscrewed to release the tissue bag 6, or a drawstring (not shown) pulled in order to release a connecting pin (also not shown). The tissue bag 6 contains a non-return valve (not shown) in order that the ribs 8 remain inflated once the supply of insufflation gas is removed.

Figure 6:
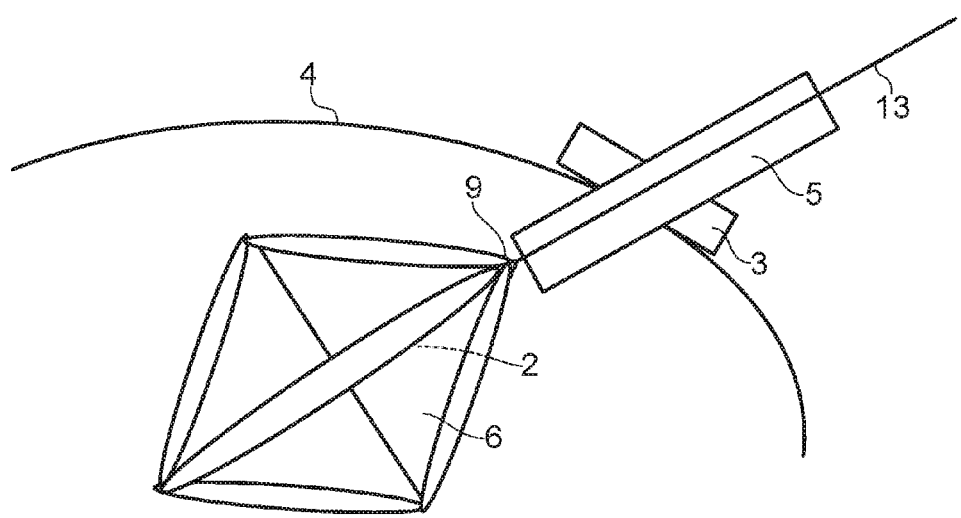

At this point, the drawstring 13 can be pulled further from within the sleeve 5, closing the opening 9, and sealing the uterus 2 within the tissue bag. This is the position shown in FIG. 6, which allows for the uterus 2 to be morcellated within the tissue bag 6, by means of a morcellating instrument (not shown) such as that described in published PCT application WO2005/112806.

Figures 7A, 7B:
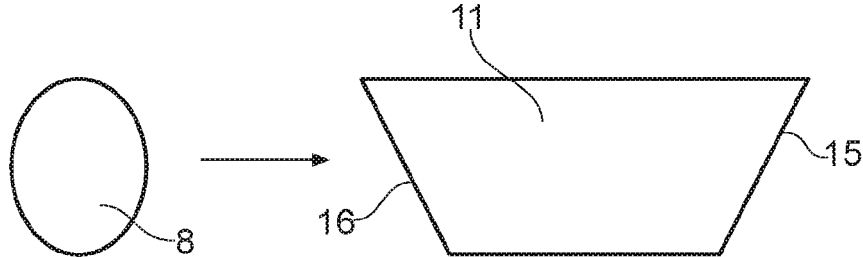
FIGS. 7A & 7B are respective cross-sectional and side views showing portions of an inflatable rib similar to those shown in the tissue bag of FIG. 1.
Figure 7C:
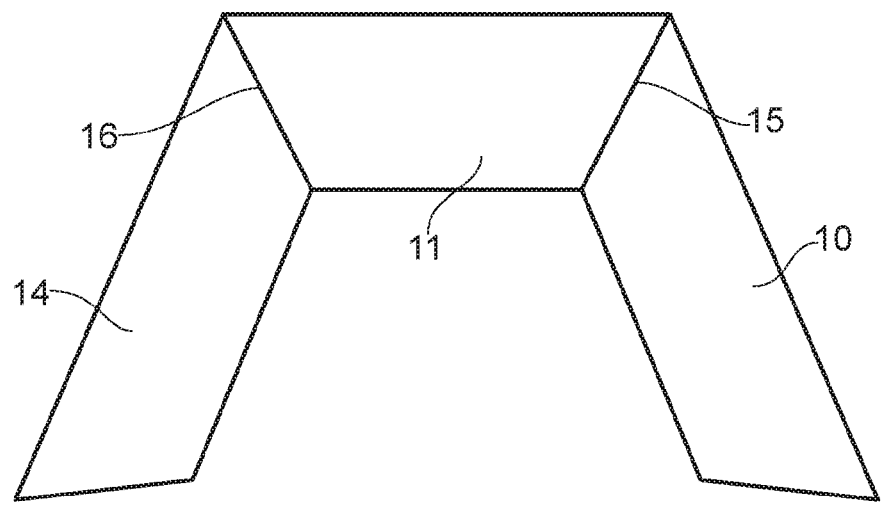
FIG. 7C is a schematic side view showing an embodiment of inflatable rib using the portions of FIGS. 7A & 7B, FIGS. 8A & 8B are schematic cross-sectional and side views showing an inflatable rib according to an alternative embodiment of tissue bag according to the invention.

FIGS. 7A, 7B & 7C show an alternative design of rib 8, in which the ribs have a circular cross-section. Ribs 8 each have first portion 10 and second portion 11 as previously described, but also a third portion 14 as shown in FIG. 7C. Between the first portion 10 and the second portion 11 is an angled end face 15, while a further angled end face 16 lies between the second portion 11 and the third portion 14. End face 15 lies at an angle of 30 degrees to the orthogonal with respect to the first portion 10. End face 15 similarly lies at an angle of 30 degrees to the orthogonal with respect to the second portion 11, such that the longitudinal axes of portions 10 & 11 differ by approximately 60 degrees when the ribs 8 are inflated.

Similarly, the end face 16 lies at an angle of approximately 30 degrees to the orthogonal with respect to the second portion 11 and the third portion 14, such that there is an angle of approximately 60 degrees between the second and third portions when the ribs 8 are inflated. In this way, as the ribs 8 are inflated, they adopt an angled formation such that the tissue bag 6 assumes a domed shape to envelope and enclose the uterus 2.

FIGS. 8A & 8B show an alternative design of the ribs 8, in which each rib has a triangular cross-section as shown in FIG. 8A. Each rib 8 has an upper edge 17 corresponding to the apex of the triangle, and a lower edge 18 corresponding to the base of the triangle. The upper edge 17 is longer than the lower edge 18, such that as the rib 8 is inflated, it is forced to assume a curved shape as shown in FIG. 8B. With each of the ribs being formed in this way, the tissue bag 6 is encouraged to assume a generally domed shape enveloping and enclosing the uterus 2 as the bag is deployed.

FIGS. 9A, 9B and 9C show a further alternative design of the ribs 8, this time once again having a circular cross-section as shown in FIG. 9A. The upper edge 17 of each rib is this time the same length as the lower edge 18, but the lower edge 18 is provided with a series of blobs of adhesive 19. Each blob of adhesive adheres to a particular local area of the tissue bag, restricting its ability to expand at that point. This means that the lower edge 18 is unable to expand as readily as the upper edge 17, resulting in the ribs 8 assuming a curved shape when they are inflated. As with the construction of FIGS. 8A & 8B, the curved shape of the ribs ensures that the tissue bag envelops the uterus 2 as the tissue bag is deployed.

Whichever of the various combinations is employed, the tissue bag 6 can be deployed over the uterus 2, and will envelop the uterus due to the shaped nature of the inflatable ribs 8. The tissue bag of the present invention provides a tissue bag which is easier to deploy, and more effective in achieving its purpose of enclosing and separating its target tissue.

Various modifications to the above described embodiments, whether by way of addition, deletion, or substitution will be apparent to the intended reader, any and all of which are intended to be encompassed by the appended claims.

The invention claimed is:

1. A tissue bag for surrounding tissue during a surgical procedure, the tissue bag comprising:
   a bag body capable of forming an enclosure;
   an opening in the bag body; and
   a first inflatable rib including a first tip and a second inflatable rib including a second tip located on the bag body, the first tip being spaced from the second tip by a first distance,
   wherein:
     inflation of the first and the second inflatable ribs to a first extent causes the bag to deploy to an open position in which the bag is capable of being placed over tissue with the tissue received through the opening, and
     inflation of the first and the second inflatable ribs to a second further extent causes the bag to envelop the tissue with the opening being smaller in diameter than in the open position and the first tip to be spaced from the second tip by a second distance that is shorter than the first distance.

2. The tissue bag according to claim 1, wherein the first and the second inflatable ribs extend longitudinally with respect to the opening.

3. The tissue bag according to claim 1, wherein the first and the second inflatable ribs extend longitudinally at equally spaced intervals around the circumference of the tissue bag.

4. The tissue bag according to claim 1, wherein the first and the second inflatable ribs each include at least first and second discrete longitudinal portions.

5. The tissue bag according to claim 4, wherein the first and second longitudinal portions are conjoined by an end face disposed at a non-orthogonal angle to the longitudinal axis of the rib.

6. The tissue bag according to claim 5, wherein the angle between the longitudinal axis of the first portion and that of the second portion is between 10 and 45 degrees.

7. The tissue bag according to claim 4, wherein the first and the second inflatable ribs each include at least first, second and third discrete longitudinal portions.

8. The tissue bag according to claim 7, wherein the second and third discrete longitudinal portions are conjoined by an end face disposed at a non-orthogonal angle to the longitudinal axis of the rib.

9. The tissue bag according to claim 8, wherein the angle between the longitudinal axis of the second portion and that of the third portion is between 10 and 45 degrees.

10. The tissue bag according to claim 1, wherein the first and the second inflatable ribs each include a longitudinal section with an upper and a lower surface, the upper surface being of a greater length than that of the lower surface.

11. The tissue bag according to claim 10, wherein the first and second inflatable ribs have a generally triangular cross-section.

12. The tissue bag according to claim 11, wherein the base of the triangle constitutes the lower surface, and the apex of the triangle constitutes the upper surface.

13. The tissue bag according to claim 1, wherein the first and the second inflatable ribs each have a generally circular cross-section.

14. The tissue bag according to claim 13, wherein the first and the second inflatable ribs each include a plurality of adhesions disposed along one longitudinal axis thereof.

15. The tissue bag according to claim 14, wherein the plurality of adhesions are equally spaced along the longitudinal axis.

16. The tissue bag according to claim 14, wherein at least some of the adhesions are formed by applying a small amount of adhesive to the rib.

17. The tissue bag according to claim 1, wherein the first and the second inflatable ribs are such that they inflate to form an arc having a radius of between 5 cm and 15 cm.

18. The tissue bag according to claim 1, wherein the opening is provided with a drawstring which can be pulled in order to close the opening.

19. The tissue bag according to claim 1, wherein the tissue bag is mounted on an elongate introducer element capable of manipulating the tissue bag into position.

20. The tissue bag according to claim 19, wherein the introducer element is provided with a lumen through which an inflation gas can be supplied to the one or more inflatable ribs.

21. A method of encapsulating tissue for surgical purposes comprising:
   introducing a tissue bag into the body of a patient, the tissue bag including:
     a bag body capable of forming an enclosure,
     an opening in the bag body, and
     a first inflatable rib including a first tip and a second inflatable rib including a second tip located on the bag body, the first tip being spaced from the second tip by a first distance;
   inflating the first inflatable rib and the second inflatable rib to a first extent such that the bag deploys to an open position;
   placing the bag over the tissue to be enclosed, with the tissue being received through the opening; and
   further inflating the first and the second inflatable ribs to a greater extent such that the first tip is spaced from the second tip by a second distance that is shorter than the first distance and the bag envelops the tissue with the opening being smaller in diameter than in the open position.

22. The method according to claim 21, further comprising pulling a drawstring to close the opening once the first and the second inflatable ribs have been inflated to envelop the tissue.

23. A method of morcellating a uterus, comprising:
   introducing a tissue bag into the body of a patient, the tissue bag including a bag body capable of forming an enclosure, an opening in the bag body, and a first inflatable rib including a first tip and a second inflatable rib including a second tip located on the bag body, the first tip being spaced from the second tip by a first distance;
   inflating the first and the second inflatable ribs to a first extent such that the bag deploys to an open position;
   placing the bag over the uterus, with the uterus being received through the opening;
   iv) further inflating the first and the second inflatable ribs to a greater extent such that the first tip is spaced from the second tip by a second distance that is shorter than the first distance and the bag envelops the uterus with the opening being smaller in diameter than in the open position; and morcellating the uterus within the tissue bag.

* * * * *